(12) United States Patent
Holvoet et al.

(10) Patent No.: US 9,839,656 B2
(45) Date of Patent: Dec. 12, 2017

(54) COMPOSITION COMPRISING SPECIFIC LACTOBACILLUS HELVETICUS STRAINS AND REDUCING FOOD AND/OR RESPIRATORY ALLERGY SYMPTOMS

(71) Applicant: NESTEC S.A., Vevey (CH)

(72) Inventors: Sebastien Holvoet, Palezieux Village (CH); Annick Mercenier, Bussigny (CH); Marietta Weiss, Palezieux Village (CH); Adrian Walter Zuercher, Bern (CH)

(73) Assignee: Nestec S.A., Vevey (CH)

( * ) Notice: Subject to any disclaimer, the term of this patent is extended or adjusted under 35 U.S.C. 154(b) by 418 days.

(21) Appl. No.: 14/372,978

(22) PCT Filed: Jan. 16, 2013

(86) PCT No.: PCT/EP2013/050695
§ 371 (c)(1),
(2) Date: Jul. 17, 2014

(87) PCT Pub. No.: WO2013/107750
PCT Pub. Date: Jul. 25, 2013

(65) Prior Publication Data
US 2015/0017143 A1  Jan. 15, 2015

(30) Foreign Application Priority Data
Jan. 19, 2012 (EP) .................................... 12151659

(51) Int. Cl.
| | |
|---|---|
| *A01N 63/00* | (2006.01) |
| *A61K 35/747* | (2015.01) |
| *A61K 38/01* | (2006.01) |
| *A23L 2/52* | (2006.01) |
| *A61K 31/702* | (2006.01) |
| *A61K 45/06* | (2006.01) |
| *A23K 10/18* | (2016.01) |
| *A23L 33/00* | (2016.01) |
| *A23L 33/135* | (2016.01) |
| *A61K 35/00* | (2006.01) |

(52) U.S. Cl.
CPC ............ *A61K 35/747* (2013.01); *A23K 10/18* (2016.05); *A23L 2/52* (2013.01); *A23L 33/135* (2016.08); *A23L 33/40* (2016.08); *A61K 31/702* (2013.01); *A61K 38/018* (2013.01); *A61K 45/06* (2013.01); *A23V 2002/00* (2013.01); *A23Y 2220/39* (2013.01); *A61K 2035/115* (2013.01)

(58) Field of Classification Search
CPC ..................................................... A01N 63/00
See application file for complete search history.

(56) References Cited

U.S. PATENT DOCUMENTS

| | | | |
|---|---|---|---|
| 6,156,353 A | 12/2000 | Beutler et al. | |
| 2003/0180272 A1 | 9/2003 | Isolauri et al. | |
| 2010/0273239 A1* | 10/2010 | Flambard | 435/252.9 |

FOREIGN PATENT DOCUMENTS

| | | | |
|---|---|---|---|
| DK | WO2005/060937 | * 7/2005 | ............... A61K 9/16 |
| JP | 2000239175 | 9/2000 | |
| JP | 2010531840 | 9/2010 | |
| JP | 2011121923 | 6/2011 | |
| WO | WO2009000875 | 12/2008 | |
| WO | WO2010124997 | 11/2010 | |
| WO | WO2011020748 | 2/2011 | |
| WO | WO2011020780 | 2/2011 | |

OTHER PUBLICATIONS

International Search Report for International Application No. PCT/EP2013/050695 dated Jun. 6, 2013.
International Written Opinion for International Application No. PCT/EP2013/050695 dated Jun. 6, 2013.
L. Van Overvelt et al., "Lactic acid bacteria as adjuvants for sublingual allergy vaccines," Vaccine, vol. 28, No. 17, Apr. 1, 2010, pp. 2986-2992, XP055030896.
G. Bu et al., "Effects of fermentation by lactic acid bacteria on the antigenicity of bovine whey proteins," Journal of the Science of Food and Agriculture, vol. 90, Jan. 1, 2010, 6 pages, XP055030894.
H. Kimoto-Nira et al., "Inhibition of leukotriene B4 production in murine macrophages by lactic acid bacteria," International Journal of Food Microbiology, vol. 129, No. 3, Feb. 28, 2009, pp. 321-324, XP025914201.
S. Kapila et al., "Immunoregulatory response of Lactobacillus helveticus fermented milk in rice," Milchwissenschaft, vol. 63, No. 4, 2008, pp. 367-369, XP009160574.
V. Taverniti et al., "The immunomodulatory properties of probiotic microorganisms beyond their viability (ghost probiotics: proposal of paraprobiotic concept)," Genes & Nutrition; Studying the Relationship Between Genetics and Nutrition in the Improvement of Human Health, Apr. 2011, vol. 6, No. 3, pp. 261-274, XP019931658.
J. Sci. Food Agric, 2010, 90, 2015-20.
Vaccine, 2010, 28, 2986-92.
Japanese Office Action for Appl No. P2014-552600 dated Sep. 3, 2016.
English Translation of Japanese Office Action for Appl No. P2014-552600 dated Sep. 3, 2016.

* cited by examiner

*Primary Examiner* — Scott Long
*Assistant Examiner* — Natalie Moss
(74) *Attorney, Agent, or Firm* — K&L Gates LLP

(57) ABSTRACT

A composition comprising specific *Lactobacillus helveticus* strains is provided for reducing the symptoms of allergies originating from food, respiratory or contact allergens. Preferably the composition reduces symptoms of allergies (secondary prevention) while also able to reduce sensitization (primary prevention).

12 Claims, 6 Drawing Sheets

Figure 1

|  | Cytokine production (% of reference) | | | |
| --- | --- | --- | --- | --- |
|  | IFNγ[a] | IL-10[b] | IFNγ/IL10 | IL-5[c] |
| L. helveticus NCC 1176 | 101.3 | 75 | 1.4 | 39.4 |
| L. helveticus NCC 2849 | 77.2 | 16 | 4.8 | 79.3 |
| L. helveticus NCC 714 | 105.0 | 37.6 | 2.8 | 38.6 |

[a] Amount of IFNγ induced by stimulation with purified E. coli LPS = 100%

[b] Amount of IL-10 induced with a reference bacterial strain with proven ability to induce IL-10 = 100%

[c] Amount of IL-5 induced in absence of any stimulation (medium) = 100%.

Figure 6

| | Cytokine production by MLN (median pg/ml ± SEM) | | | | | | | |
|---|---|---|---|---|---|---|---|---|
| | IL-4 | IL-5 | KC | IL-10 | IL-12 | TNFα | IFNγ | IL-1 | IL-2 |
| Neg Control | 5±0.4 | 16±2 | 29±1 | 72±3 | 523±40 | 9±2 | 6±1 | 12±1 | 276±19 |
| Pos Control | 61±22 | 108±69 | 156±23 | 391±125 | 672±76 | 118±20 | 619±165 | 30±5 | 677±164 |
| NCC 1176 Primary | 43±7 | 67±9 | 96±17 | 355±52 | 685±72 | 50±11 | 332±81 | 26±3 | 478±53 |
| NCC 1176 Secondary | 68±22 | 130±20 | 157±19 | 402±98 | 590±61 | 72±10 | 563±174 | 28±4 | 642±126 |
| NCC 1176 All Along | 22±10 | 61±19 | 124±16 | 217±45 | 601±61 | 36±9 | 140±89 | 21±3 | 382±64 |

COMPOSITION COMPRISING SPECIFIC *LACTOBACILLUS HELVETICUS* STRAINS AND REDUCING FOOD AND/OR RESPIRATORY ALLERGY SYMPTOMS

CROSS REFERENCE TO RELATED APPLICATIONS

The present application is a National Stage of International Application No. PCT/EP2013/050695, filed on Jan. 16, 2013, which claims priority to European Patent Application No. 12151659.5, filed Jan. 19, 2012, the entire contents of which are being incorporated herein by reference.

FIELD OF THE INVENTION

This invention relates to the use of probiotics, especially *Lactobacillus helveticus* strains in the manufacture of a composition for reducing the allergic symptoms of allergic patients when exposed to allergens.

BACKGROUND TO THE INVENTION

Allergies are among the most common health problems affecting the life of patients of all age. Allergic diseases are nowadays recognized as an epidemic by the WHO. The prevalence of allergies has been shown to increase in the past decades. Modern life style, especially urban, has been associated with high prevalence and higher severity of allergic manifestations.

Allergic sensitization in childhood, especially in early childhood and especially to food allergens, is critical and of highest interest as development of an "allergic phenotype" or "atopy" has been shown to facilitate subsequent sensitization to other allergens. Hence allergies in childhood can be the first step of an allergic cascade leading to multiple allergies later in life, a process commonly referred to as "The Atopic March". For example, it has been demonstrated in human cohorts that children with persistent food hypersensitivity early in life have a dramatically increased risk to develop allergic rhinitis (hay fever) or asthma later in childhood (Ostblöm et al Phenotypes of food hypersensitivity and development of allergic diseases during the first 8 years of life. Clin Exp Allergy. 2008 August; 38(8):1325-32). Children with milder forms of food hypersensitivity also have an increased risk for the development of respiratory allergies but to a lesser degree than children with persistent food hypersensitivity. Therefore, attenuating the severity of food hypersensitivity may be crucial for slowing down the "Atopic March".

In this context the management of allergic episodes and prevention of allergies are, in childhood and infancy, of the highest importance.

The immune system of infants is actively developing all along the few first years of life. Acting on, preventing, avoiding, managing, reducing or modulating the allergic reactions in such young patients can influence their allergic profile short term but also longer term for later in life.

Prevention of allergies can be achieved on different levels:

"Primary prevention" is the effect of preventing or reducing the risk of sensitization of patients to allergens, characterized by absence or reduced levels of allergen-specific IgE antibodies. Preventing or reducing sensitization will result in absence or reduction of allergic symptoms upon exposure to the same allergen. By modulating the way a patient becomes sensitized with regard to one allergen or one group of allergens (primary prevention), the subsequent allergic response may also be modulated.

"Secondary prevention" is the effect of modulating the symptoms of allergies, i.e. the occurrence or intensity of the allergic reaction in a patient already sensitized to one or several allergens when the patient is re-exposed to said allergen(s). By modulating the occurrence or intensity of the allergic symptoms (secondary prevention), the inconvenience and reduction in quality of life associated with allergies are minimized.

Given these distinct concepts of allergy prevention it may be hypothesized that by virtue of their inherent mechanisms of action, some compounds might act solely at one or at both of these specific levels of prevention. Some may, for example, solely reduce the sensitization to a specific allergen (primary prevention), while other compounds may solely have an effect on the secondary prevention and reduce the severity of allergic reactions. Other compounds may be able to influence both sensitization and symptoms and thus are effective in promoting primary and secondary prevention.

Food allergens are among the first allergens that infants encounter in their early life: typically, cow's milk proteins may be encountered by infants not receiving exclusive breast-feeding. Milk-proteins are indeed among the most frequently observed causes for food allergy in infancy, followed by eggs and wheat proteins. In general, food allergies can manifest by cutaneous (rash, eczema, others) and gastrointestinal symptoms (abdominal cramps; pain, especially in the abdomen; vomiting) in infants and young children. Further sensitization and episodes of allergies can also appear when the infant/young child is exposed to a novel food such as cereals, vegetables, fruits, nuts or fish or to aeroallergens such as tree or grass pollen, house dust mite or pet dander Additionally, allergic reactions can also be triggered by contact allergens.

There remains a need for specifically reducing allergic reactions and symptoms in the population of young children and infants, but also later in life. This is especially important when considering the maturation of both the intestinal and immune systems undergoing in young children and when considering the multiplicity of novel allergens that the young children are exposed to, especially around weaning.

The question of food born allergic reactions at young age is even further complicated by the specific nutritional needs of infants and young children.

Caloric intake, caloric density, variety of desirable nutrient, protein content and protein quality are all among the factors important to bring the most appropriate nutrition to infants and young children. The presence of micronutrients such as vitamins and minerals is also of importance, more specifically when their concentration is limited by specific recommended ranges corresponding to the age of the target patients. As such, for young children and infants, the matrices of food delivery are inherently complex but they are also of less variety: for example infants, although potentially allergic, usually require a specific protein balance in a matrix of milk-derived proteins. The presence of such multiple nutrients can potentiate the effect of the food allergens. In such complex matrices, low key food allergens unable to trigger allergic manifestation alone can then become more powerful at initiating an allergic reaction. Similarly compounds that may neutralize allergens or act on allergy prevention may see their effect diminished or annihilated in such complex nutritional matrices. Specifically it is not predictable whether compounds usually recognized to act on allergy prevention would still be active, and to which extend, in complex matrices such as nutritional composition for infants or young children.

There is a need to bring relief in the symptoms of food or respiratory allergies in populations of infants and young children or adults that have a history of allergic episodes and/or are allergic.

For infants and children there is a need to provide a complete nutritional composition that not only brings a variety of nutrients but also reduces the severity of allergic reactions. There is a need for providing a nutritional composition modulating the allergic reaction of young patients suffering from light to moderate forms of allergies, as these patients have special needs dictated by the incomplete maturity of their intestinal and immune systems.

There is also a need for modulating allergic reactions in young children that do not tolerate stringent pharmaceutical molecules, for example by nutritional interventions such as including modulators of the immune system into the regular nutritional regimen.

There is also a need for modulating respiratory allergy manifestations.

There is a need for providing a nutritional composition modulating the allergic reaction of young patients at the time, and around the time of weaning when the intestinal tract undergoes substantial modification and when new solid foods, potentially containing new allergenic proteins, are introduced and hence the patient is particularly susceptible to the sensitization to food allergens.

There is a need for alleviating the symptoms of allergies by providing an effective composition, possibly by reducing the exposure to intact allergens, even though the composition may not directly reduce the sensitization to allergens.

There is a need for a composition that has a positive effect on secondary prevention of allergy while not necessarily acting on the primary prevention to the same allergies.

There is finally a need for a composition, most particularly suited for young patients that by reduction of symptoms can help to diminish the "allergic phenotype" and thus can lower sensitization later in life to new allergens. There is a need for attenuating the atopic march.

SUMMARY OF THE INVENTION

In a first aspect, the present invention provides a composition for use in reducing the symptoms of allergies originating from food in patients having allergies triggered by food allergens, especially in young patients, children, babies and infants. The composition may be a complete nutritional composition.

The composition may also be used in reducing the symptoms of respiratory allergies.

While the composition of the present invention is applicable for young patients, it may also be successfully used in adult patients.

In a second aspect, the present invention provides a composition that promotes secondary prevention of allergic reactions triggered by food allergens, optionally while not affecting the primary prevention against the same allergens.

In a third aspect, the present invention provides a composition that comprises specific probiotics, especially those belonging to the *Lactobacillus* genus, namely the strains *L. helveticus* NCC 1176, and/or NCC 714.

In another aspect of the invention the composition of the invention is especially effective for infants/young children at the time of weaning.

The invention further extends to reduction of the sensitization to other allergens later in life.

BRIEF DESCRIPTION OF THE DRAWING

FIG. 1: Cytokine secretion profile of Th2-skewed human PBMC after co-culture with *L. helveticus* NCC 1176, NCC 2849 or NCC 714.

FIG. 6: Cytokine production by mesenteric lymph nodes (LN) lymphocytes and splenocytes restimulated ex vivo.

DETAILED DESCRIPTION OF THE INVENTION

Definitions

Figure 2:
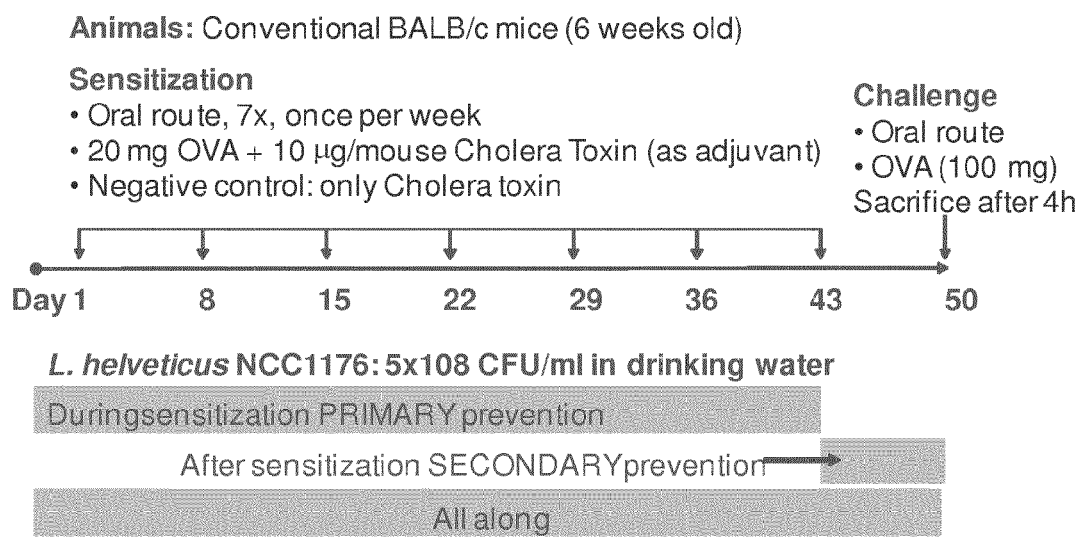
FIG. 2: Schematic description of OVA food allergy mouse model

In this specification, the following terms have the following meanings:

"Complete nutritional composition". For the purpose of this document a complete nutritional composition is a composition that comprises a significant amount, usually 50% or more, of the major nutritional nutrients recommended for a given age. Such major nutrients are usually provided in quantity and proportion such as to fulfil 50% or more of the specific recommended nutrient's doses for a given age, when used in adequate quantity for providing the recommended caloric intake for a given age. A complete nutritional composition usually comprises a source of protein, a source of lipid, a source of carbohydrates in a balanced proportion that meets the general recommendation for a given age. It usually also include micronutrients such as vitamins and minerals, as well as a source of essential amino acids and a source of essential fatty acids. It is however understood that a complete nutritional composition may neither comprise all specific nutrients, nor all recommended amounts, to fulfil all nutritional needs of an infant or young child. A complete nutritional composition excludes compositions comprising merely *Lactobacillus* in a predominant proportion.

"Symptoms of allergies" generally include symptoms triggered by allergens. Such symptoms include cutaneous (redness of skin, rash, itchiness, dermatitis, eczema), ocular (itching and watering of the eyes), gastrointestinal (congestion, abdominal pain, cramps, vomiting diarrhea), respiratory (itching of the nose, nasal congestion, rhinitis, asthma) and in severe cases systemic (dizziness, mental confusion, anaphylaxis) manifestations.

"Primary prevention of allergies" means all measures aiming at avoidance or reduction of allergic (immunological) sensitization for example prevention or reduction of allergen specific IgE antibodies.

"Secondary prevention of allergies" means prevention or reduction of the development of allergic disease/allergic symptoms in a sensitized individual.

"Weaning period" is the period during which infants are adapting from pure liquid nutrition to solid or semi-solid food, and adapting from quasi unique food type (generally mother milk or infant formula) to a variety of foods.

"Sensitization" means induction/development of allergen-specific IgE antibodies.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10). The definition of probiotic is generally admitted and in line with the WHO definition. The probiotic can comprise a unique strain of micro-organism, of a mix of various strains and/or a mix of various bacterial species and genera. In case of mixtures the singular term "probiotic" can still be used to designate the probiotic mixture or preparation.

"Prebiotic" generally means a non digestible food ingredient that beneficially affects the host by selectively stimulating the growth and/or activity of micro-organisms present in the gut of the host, and thus attempt to improve host health.

*Lactobacillus helveticus* (*L helveticus*) strain NCC 1176 (Nestlé Culture Collection reference 1176), is also named LH91 and was deposited with the INSTITUT PASTEUR, 25 rue du Docteur Roux, F-75724 PARIS Cedex 15 on October 1991 as CNCM I-1156.

*Lactobacillus helveticus* (*L helveticus*) strain NCC 2849 (Nestlé Culture Collection reference 2849), was deposited with the INSTITUT PASTEUR, 25 rue du Docteur Roux, F-75724 PARIS Cedex 15 on December 2008 as CNCM I-4095.

*Lactobacillus helveticus* (*L helveticus*) strain NCC 714 (Nestlé Culture Collection reference 714), was deposited with the INSTITUT PASTEUR, 25 rue du Docteur Roux, F-75724 PARIS Cedex 15 on October 1991 as CNCM I-1154.

The inventors have evidenced that allergic reaction and symptoms can be alleviated when sensitized young mammals are administered *L. helveticus* NCC 1176 or NCC 714. This administration may be in the form of a complete nutritional composition comprising *L. helveticus* NCC 1176 or NCC 714. This defined a positive effect on the secondary prevention of allergies. This effect was accompanied by a reduction of the sensitization of the young mammals to allergens (i.e. primary prevention of allergies was evidenced).

Notably, this effect can not be generalized over all *L. helveticus* strains, as evidenced by *L. helveticus* NCC 2849, which exhibits an entirely different behaviour. Hence, these findings are a further example of the strain specificity of the health benefits of probiotics.

Effect of the Composition:

The invention relates to the use of micro-organisms of the genus *Lactobacillus*, more particularly *Lactobacillus helveticus* (*L. helveticus*), and more specifically the strains *L. helveticus* NCC 1176 and NCC 714 in the manufacture of a composition to reduce the symptoms in patients having allergies triggered by food, respiratory and/or contact allergens. The composition may be a complete nutritional composition, for example. The inventors have evidenced that consumption of *Lactobacillus helveticus* NCC 1176, or NCC 714 have a particular pronounced effect in reducing symptoms of food allergy in a group of mice receiving a nutritional composition containing said *Lactobacillus* strains. The model mimics food allergy in humans, when humans (typically infants/young children) are naturally sensitized to food allergens and are further re-exposed to said allergens.

The bacterial strains *L. helveticus* NCC 1176 and NCC 714 hence show a protective effect.

In one embodiment of the invention the effect of the composition is more specifically an effect on the secondary prevention of allergies. The symptoms of allergies, in the mouse model, are indeed reduced significantly, as illustrated by a lower allergic clinical score. Generally the symptoms can include all or a selection of the usually recognized symptoms of allergies.

The symptoms may comprise diarrhea, skin irritation or respiratory symptoms or combinations thereof. The symptoms may also be accompanied by a release of biochemical mediators, such a tryptase, chymase, histamine, leukotriens.

The composition may also have an effect on the sensitization of the patients to the allergens. Indeed a primary prevention of allergies is achieved by the composition comprising *L. helveticus* NCC 1176. The animals exhibited a lower sensitization to food allergens. The effect of the composition is in that regard of high interest as it both reduces the symptoms and reduces the sensitization, i.e. the risk of later symptoms upon re-exposure to allergens.

The composition of the present invention may be used to reduce the sensitization to other allergens later in life. It is believed that the composition promotes (or at least does not block) the natural processes of immune maturation and hence, is able to have a long term effect on lowering the sensitization to the same allergens or to different allergens (reduction of sensitization later in life). By reducing the symptoms of allergy (secondary prevention) and the short term sensitization (as part of the primary prevention), it is hypothesized that the composition of the invention can still allow for the natural immune maturation to occur, and have such long term beneficial effect.

Composition of the Invention or for Use in the Invention:

The composition of the invention may be a nutritional composition, a food, a drink, a food additive, a nutraceutical, a pet food product, an infant formula, an infant cereal or a baby food, for example.

The composition may be a complete nutritional composition such as an infant formula or can bring a substantial portion of the complete diet or can be a nutritional complement. For infants and children, preferably the composition is a complete nutritional composition that brings all or almost all the nutritional requirements of the target body when taken as the sole source of nutrient. In another embodiment, such as a baby food, the composition brings a portion of the complete diet, preferably more than 50% (quantitatively and qualitatively). In one embodiment the composition comprises infant cereals.

For example, if the composition is intended for consumption by adults the composition may be a yoghurt or a fermented milk drink.

To the inventors best knowledge this is the first time that a *Lactobacillus helveticus* strain was described with the above mentioned effects. As different probiotics of a different genus or a different species may have very different effects on taste, for example, and may have different requirements for cultivation and storage there is a clear desire to have available a *Lactobacillus helveticus* strain with the above benefits. Consequently, the present invention relates in particular to the strains *L. helveticus* NCC 1176 and/or NCC 714.

The composition may comprise between $10^4$ and $10^{11}$ colony forming units (CFU) per g of the dry composition. When the composition is an infant formula the amount of probiotic in the infant formula may be between $10^5$ and $10^8$ CFU/g of infant formula. The composition may comprise between $10^6$ and $5 \times 10^7$ CFU/g, that is in a dose demonstrated to have a physiological effect. It has been identified that probiotics at a low dose can have a beneficial effect, in particular when the composition also comprises prebiotics and proteins in a defined limited amount. In such embodiment the probiotics may be present in the composition in an amount between $10^3$ and $10^5$ CFU/g. The prebiotics, for example in the form of oligosaccharides and/or the proteins can be present in an amount not exceeding 4 g/100 kcal or less than 2 g/100 kcal or less than 1.8. g/100 kcal or less than 1.5 g/100 kcal of the composition.

The probiotic can be mixed together with the dry or wet composition of the invention. Treatments or specific processes can be applied to improve the stability or viability of the probiotics in the composition. The probiotic can be applied in a dry form or in a wet from. After mixing the probiotic with the composition the mix can be processed in a way that does not dramatically affect the viability of the probiotics. In another embodiment the probiotics are partly inactivated before, during or after the mixing. In one embodiment the probiotics have been rendered inactivated and/or incapable to replicate prior to the use in the composition of the invention. This for example can be achieved by heat treatment or other described treatments.

The composition may comprise prebiotics. It is known that prebiotics comprise carbohydrates and more specifically, oligosaccharides. Furthermore it is known that they have widely been used as functional food ingredients. They resist hydrolysis by enzymes of the human digestive tract, can reach the colon undegraded and provide a carbohydrate substance particularly suited to the growth of bifidobacteria or other probiotics. Oligosaccharides may for example be produced from glucose, galactose, xylose, maltose, sucrose, lactose, starch, xylan, hemicellulose, inulin, or a mixture thereof. Purified commercially available prebiotic products such as fructooligosaccharides contain greater than about 95% solids in the form of oligosaccharides.

Preferably, an embodiment of the composition is a nutritional composition which comprises at least one prebiotic.

Preferably, an embodiment of the prebiotic comprises an oligosaccharide produced from glucose, galactose, xylose, maltose, sucrose, lactose, starch, xylan, hemicellulose, inulin, or a mixture thereof. More preferably the oligosaccharide comprises fructooligosaccharide. Most preferably the prebiotic comprises a mixture of fructooligosaccharide and inulin. Preferably this mixture comprises PREBIO1® or a mixture of commercially available RAFTILOSE® and RAFTILINE®.

Preferably, the prebiotic component of the composition may comprise about 50% to about 90% fructooligosaccharide. More preferably it comprises about 60% to about 80% fructooligosaccharide. Most preferably it comprises about 70% fructooligosaccharide. The prebiotic may comprise about 10% to about 50% inulin, or about 20% to about 40% inulin, or about 30% inulin. For example, the prebiotic component may represent about between 0.1% and 10% of the composition.

The composition of the present invention may further comprise an apple extract comprising, or enriched in polyphenols. The apple extract helps, e.g., reducing the symptoms of allergies originating from food in patients having allergies triggered by food allergens. As such the apple extract acts in a synergistic way in concert with the probiotic to modulate, reduce, or attenuate allergies in patients having food allergies. Such a composition may be used for baby food and/or baby cereals that naturally represent a suitable carrier for the composition. The baby food or baby cereal may inherently comprise apple extracts or material from apple.

Hypothetical Mechanism of Action:

Allergic diseases have steadily increased over the past decades and they are currently considered as epidemics by WHO. In a general way, allergy is considered to result from an imbalance between the Th1 and Th2 responses of the immune system leading to a strong bias towards the production of Th2 mediators. Therefore, without being bound by the theory, it is hypothesized that allergy can be mitigated, down-regulated or prevented by restoring an appropriate balance between the Th1 and Th2 arms of the immune system. This implies the necessity to reduce the Th2 responses or to enhance, at least transiently, the Th1 responses. The former could be characterized by reduced production of Th2 cytokines such as IL-5, the latter could be characterized by increased production of Th1 cytokines such as IFNγ. Alternatively, in a sensitized individual, a general anti-inflammatory effect may be most desirable, e.g. through the induction of T-regulatory (Treg) cells, capable of down-modulating the effects of both Th1 and Th2 cells. This could be indicated by the ability of inducing secretion of IL-10.

The composition of the present invention may comprise hydrolyzed or partially hydrolyzed proteins. A nutritional composition based on (partially) hydrolyzed proteins is particularly suited to the immune system and gastro-intestinal tract of infants/young children because hydrolyzed proteins are more easily digested and have reduced allergenicity compared to intact proteins. Furthermore, without being bound by theory it can be hypothesized that hydrolyzed proteins might be a preferable substrate for probiotics or intestinal bacteria (especially those displaying a variety of peptidase activities) compared to intact proteins, leading to an improved effect of the probiotic strain and thus synergism between hydrolyzed proteins and probiotics. This represents a most appropriate composition for the immune system and gastro-intestinal tract of a food-allergic infant/young child. In such instance the combination of *L. helveticus* NCC 1176 and/or NCC 714 with hydrolyzed proteins is of relevance to the invention.

In one embodiment the hydrolyzed proteins are proteins hydrolyzed from whey and/or casein. The hydrolyzed proteins may result from the action of trypsin and/or chymotrypsin on the proteins (esp. whey proteins The hydrolyzed proteins may comprise soy proteins, wheat proteins or/and egg proteins. For example, the hydrolyzed proteins may result from the action of proteases such as Protamex® and/or Flavourzyme® (Novozyme, Denmark). The proteins of the composition, preferably the hydrolyzed proteins, may comprise cereal or egg proteins. In one embodiment the hydrolyzed proteins may result from the action of Alcalase. The composition of the invention may comprise a mix of two or more of the cited protein sources.

Target Group:

The composition of the invention is most suitably targeted at relatively young patients, but appropriate compositions can be designed as foods, drinks or nutritional complements for adults, with the same effect.

Preferentially indeed the patients are sufficiently young to still go through a maturation phase of their immune system and their gastro-intestinal tract. In such patients the effect of the composition can be more intense or more rapid. In one embodiment the composition is an infant formula, infant cereal and/or a baby food. Preferably the composition is targeted at young humans below the age of 6 years, between birth and the age of 3 years or between birth and weaning.

In one embodiment the composition is a starter or a follow-up infant formula. Preferably the nutritional composition comprises a vast majority of the necessary nutrients for the feeding of the young humans.

In one embodiment the nutritional composition is an infant cereal composition for infants/young children 1 to 4 years old. The composition can be more specifically targeted to and administered during the weaning period and/or up to 12 months thereafter. The weaning period is indeed important in regard to the invention as the infants are exposed to a variety of foods during the weaning period, while still undergoing maturation and re-organisation of their immune system and their gastro-intestinal tract. Effective control of the allergic response is therefore of particular importance during that period.

In regard to the use of the composition of the invention the children, babies or infants may be allergic children. Allergic children are those children, babies or infants having experienced at least one episode of allergic reaction—light, moderate or severe—to an allergen, for example a food, respiratory or contact allergen. In one embodiment of the invention the children, babies or infants have declared severe allergies to food allergens and/or have experienced more than one moderate or severe episode of food allergy. The symptoms of allergies can include various known symptoms such as cutaneous irritation or redness, gastro-intestinal symptoms or respiratory symptoms.

The composition of the present invention may also be used for older children including adolescent up to 18 years old or for adults.

The food allergens encompassed by the present invention can include all types of allergens naturally occurring or usually occurring in food, especially food for young humans (e.g. infants, babies, children). Specific examples of typical food allergens are milk, eggs, fish (e.g., bass, flounder, cod), Crustacean shellfish (e.g., crab, lobster, shrimp), tree nuts (e.g., almonds, walnuts, pecans), peanuts, wheat, or soybeans.

The respiratory allergens encompassed by the present invention can include all types of respiratory allergens. Typical respiratory allergens are for example dust mites, rye, ragweed, cockroaches, pollen, mold, animal dander, or dust.

The contact allergens encompassed by the present invention can include all types of contact allergens. Typical contact allergens are for example nickel, gold, fragrance mixes, thimerosal, neomycin sulphate, formaldehyde, cobalt chloride, bacitracin, or Quaternium 15.

Experimental Results:

Probiotics have been tested in human and animal trials for their ability to interfere with allergic sensitization or with development of allergic symptoms in sensitized individuals. Here it was demonstrated that particular strains of *L. helveticus*, namely *L. helveticus* NCC 1176 and NCC 714, have a potential to mitigate the development of allergic sensitization or symptoms.

An in vitro system based on human blood lymphocytes was developed to determine cytokine profiles induced by different strains of *L. helveticus*. It is hypothesized that the observed profiles are predictive for cytokine production induced in vivo by the same strains and thus for the biological effects conferred by said strains.

Cells of an allergic individual or of an individual prone to allergy development are characterized by their propensity to produce Th2 cytokines. To partly mimic this status in vitro, a cell culture model of Th2-skewed human peripheral blood mononuclear cells (PBMC) was developed as an alternative to using PBMC of allergic donors. Th2-skewing was induced by culturing PBMC with interleukin (IL)-4+anti-CD40 antibody (as detailed in Methods); after 3 days of culture to induce Th2-skewing, lactobacilli were added for an additional 48 hours, resulting in a total culture duration of 5 days. As a basic read-out the cytokines IFNγ, IL-10 and IL-5 were measured by ELISA in the supernatant of cells stimulated with *L. helveticus* strains.

FIG. 1 shows that *L. helveticus* NCC 1176 and *L. helveticus* NCC 714 (henceforth called NCC 1176 and NCC 714) induced similar amounts of IFN-γ (101.3% and 105%) that were higher than that induced by NCC 2849 (77.2%). NCC 1176 induces more IL-10 than NCC 714 and NCC 2849. However ratios of IFN-γ/IL-10 were lower for NCC 1176 and NCC 714 (1.4 vs 2.8) than for NCC2849. In addition, NCC 1176 and NCC 714 were efficient inhibitors of IL-5 secretion. These data suggest that these 2 strains are producers of IFNγ and IL-10 under Th2-skewed conditions and are able to inhibit Th2 cytokines production by PBMC in contrast to strain NCC 2849. Therefore NCC 1176 and NCC 714 will have an anti-allergic effect through their anti-inflammatory activity.

The in vivo effect of *L. helveticus* NCC 1176 was tested as an example in a mouse food allergy model (OVA Food Allergy Mouse Model, illustrated in FIG. 2).

BALB/c mice were sensitized at weekly intervals with ovalbumin (OVA)+cholera toxin by the oral route during 7 weeks. In this model, an oral challenge with a large dose of OVA at the end of the sensitization period lead to clinical symptoms such as diarrhoea, scratching episodes, bristled fur, cyanosis and loss of mobility.

NCC 1176 was given to mice via drinking water ($5 \times 10^8$ CFU/ml; ad libitum) either during the sensitization phase from day 1 to 43 (primary prevention), during the last week of the experiments (day 43-50; secondary prevention) or all along the trial (day 1-50, all along).

Figure 3:
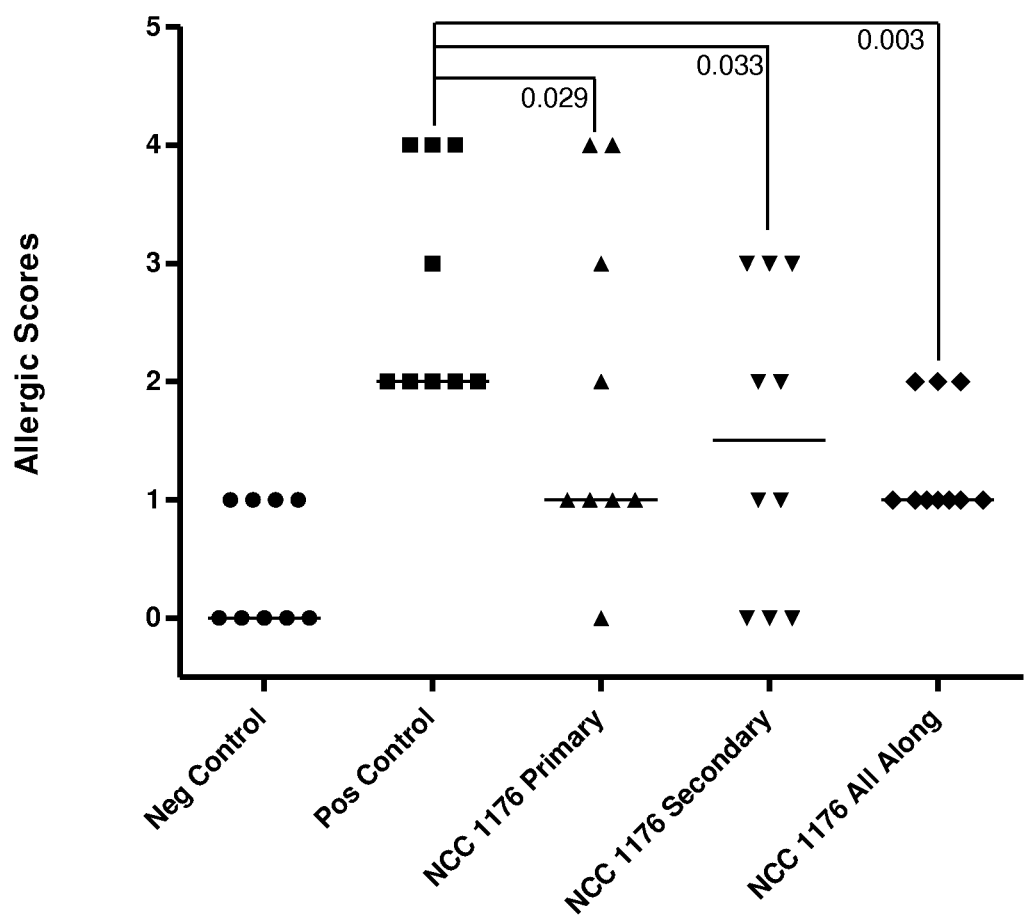
FIG. 3: Illustration of the clinical score showing reduced symptoms of food allergy in mice receiving $5\times10^8$ CFU/ml of *L. helveticus* NCC 1176 in drinking water. Symbols represent individual mice, bar indicates median.

FIG. 3 shows the clinical symptoms. Mice treated with NCC 1176 developed significantly less severe clinical symptoms after challenge than sensitized, untreated animals (positive control). The effect of NCC 1176 significantly decreased the clinical symptoms when administered either during sensitization (NCC 1176 Primary) or after sensitization (NCC 1176 Secondary). However the beneficial effect was most pronounced when NCC 1176 was administered throughout the whole experiment in the animal model (NCC 1176 All Along.

Figure 4:
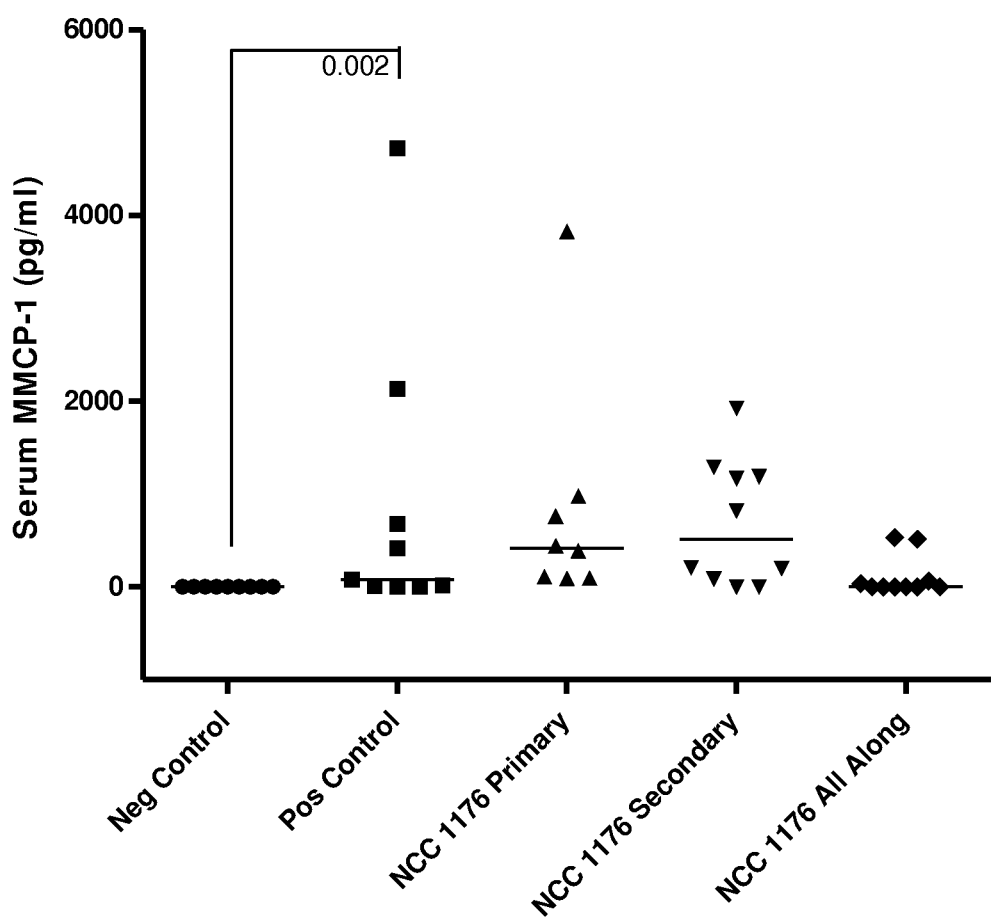
FIG. 4: Serum levels of Mouse Mast-Cell Protease 1 (MMCP-1) in sera 4 hours after challenge. Symbols represent individual mice, bar indicates median.

As shown in FIG. 4, in addition to the clinical score, mouse mast-cell protease 1 (MMCP-1) serum levels were determined as a measure of intestinal mast-cell activation by allergen challenge. OVA challenge led to a strong increase of serum levels of MMCP-1 in the positive control compared to the negative control group. A trend in the modulation of MMCP-1 serum levels (although not significant) was observed in mice treated with NCC 1176, compared to the positive control group.

Figure 5:
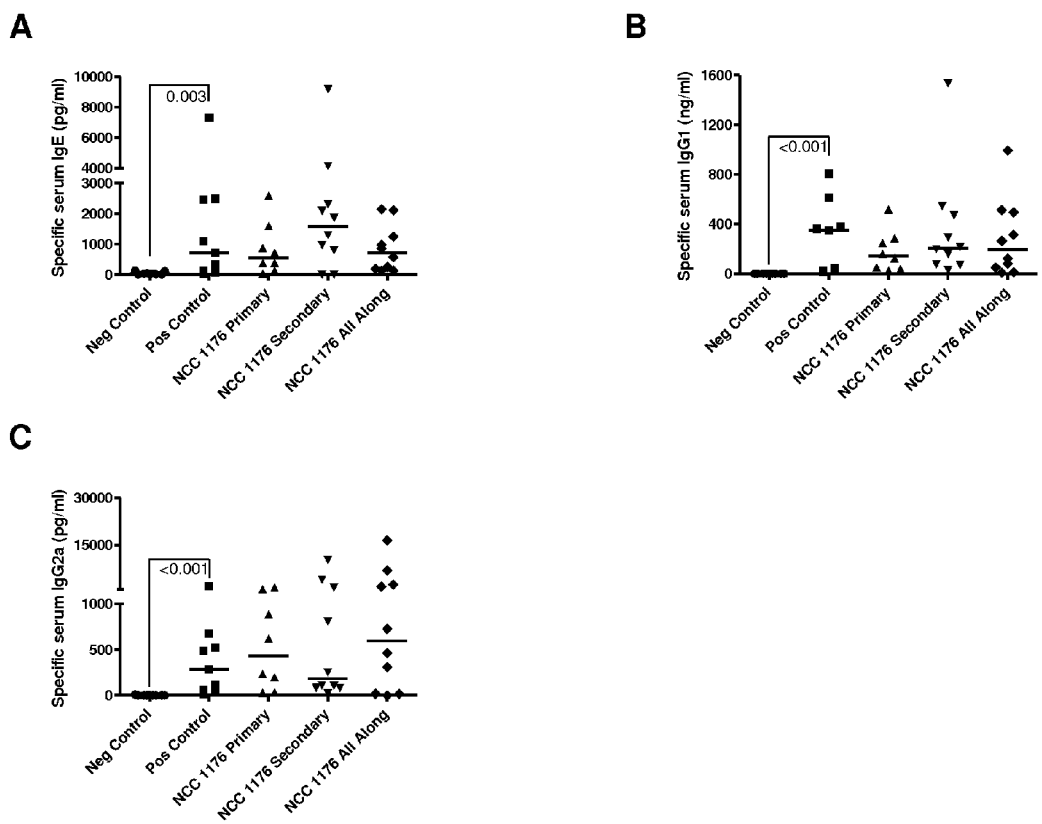
FIG. 5: Dot plot representation of OVA-specific IgE, IgG1, IgG2a in sera 4 hours after challenge measured by ELISA. Solid line corresponds to median.

FIG. 5 shows that OVA-specific serum IgE, IgG1 and IgG2a levels were increased in sensitized mice (Pos. Control) vs. non-sensitized mice (Neg. Control). The treatment with NCC 1176 during the sensitization phase (primary prevention or all along) resulted in slightly reduced serum levels of OVA-specific IgE (FIG. 4A), IgG1 (FIG. 4B), while IgG2a (FIG. 4C) remained not affected. In contrast, treatment just before the challenge (secondary prevention) did not affect the levels of specific serum IgE and IgG1 as expected.

FIG. 6 shows the cytokine production by ex vivo restimulated lymphocytes. For this purpose, lymphocytes from mesenteric lymph nodes (MLN) were collected after challenge, restimulated with 1 mg/ml of OVA and cultured for 72 hours. Levels of IL-4, IL-5, KC, IL-10, IL-12, TNFα, IFNγ, IL-1 and IL-2 were measured by multiplex assay (Mesoscale®). MLN lymphocytes of mice treated with NCC 1176 in primary prevention produced less IL-4, IL-5, KC, TNFα, IFNγ and IL2 compared to the Positive Control (Tab. 2). In mice treated all along with NCC 1176, MLN restimulation lead to a decrease of IL-4, IL-5, IL-10, TNFα, IFNγ and IL-2. The cytokine profile of mice treated with *L. helveticus* NCC 1176 just before the challenge did not differ substantially from the positive control group.

Conclusion: These data show that consumption of *L. helveticus* NCC 1176 and/or NCC 714 leads to reduced symptoms (primary, secondary prevention) in a mouse food allergy model. This can be achieved by consuming NCC 1176 and/or NCC 714 all along the sensitization phase up to the end of the experiment. The effect is more profound when NCC 1176 and/or NCC 714 is consumed all along the experiment. However, symptoms were still reduced when the strain was consumed only in preventive or in treatment phase. This suggests that NCC 1176 has the ability to impact both on the sensitization process as well as effective mechanism that are responsible for allergic symptoms. As *L. helveticus* NCC 714 exhibits the same in vitro immune characteristics than *L. helveticus* NCC 1176, it is expected to behave in a similar way in vivo and thus to display the same anti-allergy properties, in contrast to *L. helveticus* NCC 2849.

Analytical Methods:
Reagents and Bacterial Biomass:

Bacterial biomass was produced by culture of each strain under optimal conditions in MRS medium). Growth kinetics were determined for each strain and according to these, biomass was harvested 3 h after reaching the stationary phase. At this time-point cultures were washed 2× in cold PBS and frozen in PBS 20% glycerol at −80° C. in 50 μl aliquots. LPS (from *E. coli*) was purchased from Sigma (Buchs, Switzerland).

Isolation and Culture of Th2-Skewed Human PBMC:

Human peripheral blood mononuclear cells (PBMC) were isolated from filters obtained from the "Centre de Transfusion of the CHUV". The cells trapped in the filters were flushed back into the blood collection bag with 90 ml of Hanks balanced salt solution (HBSS) (Sigma). The cells were diluted 1:2 with HBSS and the PBMC were isolated by density gradient centrifugation on Histopaque 1077 (Sigma). The cells at the interphase were collected and washed two times with HBSS. The PBMC were resuspended in Iscove's Modified Dulbecco's Medium (cIMDM) (Sigma) complemented with 10% fetal bovine serum FBS (Bioconcept, Paris, France), 1% L-glutamine (Sigma), 1% Penicillin/Streptomycin (Sigma) and 0.1% Gentamycin (Sigma). The cells were cultured in 48 wells plate (Milian, Meyrin, Switzerland) at $1.5 \times 10^6$ cells/ml in the presence of 50 ng/ml of IL-4 (Bioconcept) and 1 μg/ml of anti-CD40 antibody (R&D Systems, Abington, England) in cIMDM to induce a Th2 cytokine phenotype. LPS was used at 1 μg/ml. After 3 days of culture, probiotics were added at $10^7$, $10^6$, and $10^5$ CFU/ml. After adding ingredients, PBMC culture was continued for an additional 48 h resulting in total culture duration of 5 days.

Cytokine ELISA:

Human IFN-γ, human IL-5, human IL-10, mouse IFN-γ, mouse IL-13, and mouse IL-10 cytokines were measured using DuoSet kits from R&D systems according to the manufacturer's instructions.

Evaluation of ELISA Results:

OD values were transformed into pg/ml using the standard curves. To adjust for the large donor-to-donor variation generally observed with PBMC from different human donors, data were standardized according to an arbitrary internal standard. The pg/ml value of IFN-γ obtained for each donor by stimulation with LPS was set to 100%. For normalization of IL-10 values, the amount of IL-10 induced with strain *B. lactis* NCC 2818 (deposited by Nestec SA under CNCM-13446) was considered as 100%. Finally, the amount of IL-5 induced with IL-4 and anti-CD 40 antibody in medium only (i.e. in the absence of probiotics) was set to 100%.

OVA Food Allergy Mouse Model:

All studies were approved by a Nestec internal Ethics Committee and the Service Vétérinaire of the Canton of Vaud, Switzerland (Authorization #1970). Six weeks old female conventional BALB/c mice (Harlan Laboratories, France) were sensitized by the oral route (with a gavage needle) at weekly intervals with 20 mg of Ovalbumin (OVA) from Fluka (Buchs, Switzerland)+10 μg/mouse of Cholera toxin (used as adjuvant; List Biologicals, purchase from LuBioscience, Lucerne, Switzerland) during 7 weeks. One week after the last sensitization an oral challenge with 100 mg of OVA was performed. Nutritional intervention with *L. helveticus* NCC 1176 ($5 \times 10^8$ CFU/ml in drinking water) was done at different phases of the experiment; for primary prevention during sensitisation period, for secondary prevention starting at the end of the sensitization phase, or all along the trial (FIG. 3). Starting 30 minutes after challenge mice were individually observed for 30 min. Clinical symptoms were recorded and quantified as follows (Allergic Score): 0: no symptoms, less than 4 episodes of scratching; 1: 4-10 episodes of scratching around the nose and head, no diarrhoea; 2: more than 10 episodes of scratching or bristled fur and immobility or soft stool; 3: diarrhoea or laboured respiration or cyanosis; 4: diarrhoea in combination with immobility after prodding, bristled fur, laboured respiration or cyanosis; 5: anaphylaxis. Four hours after challenge mice were sacrificed (cervical dislocation), blood and the last centimeter of ileum was taken and frozen in liquid nitrogen.

Serum MMCP-1:

Murine mast cells protease 1 (MMCP-1) was quantified in mouse serum by ELISA, purchased from Moredun Scientific (Penicuik, Scotland) according to the manufacture's instructions. The MMCP-1 concentration was obtained by converting OD values in pg/ml using a polynomial standard curve.

Isolation and Culture of Mesenteric Lymph Node Cells:

Mesenteric lymph nodes (MLN) were homogenized with the plunger of a syringe in a cell strainer (BD Falcon, Milian, Meyrin Switzerland). Cells were centrifuged and washed two times in RPMI (Sigma) complemented with 10% of fetal bovine serum FBS (Bioconcept, Paris, France), 1% L-glutamine (Sigma), 1% Penicillin/Streptomycin (Sigma), 0.1% Gentamycin (Sigma), 0.1% β-mercaptoethanol (Sigma). Cells were cultured in 96 well flat bottom plate (Corning, Milian) in the absence or presence of OVA (1 mg/ml) with $3 \times 10^6$ cells/ml. After 72 h of culture plates were frozen.

Cytokines in Supernatant of MLN Cultures:

Mouse IL-4, IL-5, IL-10, IFN-γ, IL-1β, IL-2, IL-8, TNF-α, IL-12T were measured using the mouse Th1/Th2 9-plex multiplex kit (Meso Scale Discovery, Gaithersburg, Md., USA) according to the manufacture's instructions.

Example 1

An example of the composition of an infant formula for use according to the present invention is given below. This composition is given by way of illustration only. The protein source is a conventional mix of whey protein and casein.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| Lactobacillus helveticus (NCC 1176); see experimental part | $2 \times 10^7$ CFU/g of powder | |

The invention claimed is:

1. A method for reducing the symptoms of allergies in patients having allergies triggered by food, respiratory or contact allergens, the method comprising administering a composition comprising an apple extract comprising polyphenols and at least one Lactobacillus helveticus strain selected from the group consisting of Lactobacillus helveticus NCC 1176, Lactobacillus helveticus NCC 714 and combinations thereof to an individual in need of same.

2. The method of claim 1, wherein the composition provides secondary prevention against allergic reactions triggered by food, respiratory or contact allergens.

3. The method of claim 1, wherein the composition has an effect on the sensitization of the patients to the food, respiratory or contact allergens.

4. The method of claim 1, wherein the composition comprises between $10^5$ and $10^8$ colony forming units (CFU) Lactobacillus helveticus per gram of dry composition, and/or between $10^6$ and $10^{13}$ colony forming units (CFU) Lactobacillus helveticus per daily dose.

5. The method of claim 1, wherein the composition comprises at least one prebiotic.

6. The method of claim 1, wherein the composition comprises cereal proteins and/or hydrolyzed proteins.

7. The method of claim 1, wherein the composition reduces the sensitization to other allergens later in life.

8. The method of claim 1, wherein the symptoms are selected from the group consisting of gastro-intestinal, cutaneous, respiratory, and combinations thereof.

9. The method of claim 1, wherein the composition is in a form selected from the group consisting of a nutritional composition, a food, a drink, a food additive, a nutraceutical, a pet food product, an infant formula, an infant cereal and a baby food.

10. The method of claim 1, wherein the individual is 1 to 4 years old.

11. The method of claim 1, wherein the composition is to be administered to infants during the weaning period and/or up to 12 months thereafter.

12. The method of claim 1, wherein the symptoms are accompanied by release of biochemical mediators.

* * * * *